(12) United States Patent
Hee

(10) Patent No.: US 7,609,503 B2
(45) Date of Patent: Oct. 27, 2009

(54) INSULATED METAL GROUNDING BRACELET

(76) Inventor: Roland Hee, 88-11-01 Silverton Condominium, Gurney Drive, Penang (MY) 10250

(*) Notice: Subject to any disclaimer, the term of this patent is extended or adjusted under 35 U.S.C. 154(b) by 169 days.

(21) Appl. No.: 11/938,695

(22) Filed: Nov. 12, 2007

(65) Prior Publication Data

US 2009/0122457 A1 May 14, 2009

(51) Int. Cl.
*H01H 47/00* (2006.01)
(52) U.S. Cl. .................. 361/220; 361/212; 361/223; 361/224; 439/37; 57/901
(58) Field of Classification Search ................ 361/212, 361/220, 223–224; 439/37; 57/901
See application file for complete search history.

(56) References Cited

U.S. PATENT DOCUMENTS

| | | | |
|---|---|---|---|
| 1,531,862 | A | 3/1925 | Larned |
| 2,586,747 | A | 2/1952 | Van Atta et al |
| 2,928,100 | A | 3/1960 | Gagnon |
| 2,955,234 | A | 10/1960 | Price |
| 2,998,697 | A | 9/1961 | Augenstein |
| 3,063,447 | A | 11/1962 | Kirsten |
| 3,237,395 | A | 3/1966 | Bennett |
| 3,377,509 | A | 4/1968 | Legge |
| 3,422,460 | A | 1/1969 | Burke et al |
| 3,424,698 | A | 1/1969 | Lupinski et al |
| 3,459,997 | A | 8/1969 | Legge |
| 3,541,389 | A | 11/1970 | Van Name |
| 3,582,448 | A | 6/1971 | Okuhashi et al |
| 3,596,134 | A | 7/1971 | Burke |
| 3,699,590 | A | 10/1972 | Webber et al |
| 3,810,258 | A | 5/1974 | Mathauser |
| 3,812,861 | A | 5/1974 | Peters |

(Continued)

FOREIGN PATENT DOCUMENTS

DE 2547390 10/1975

(Continued)

OTHER PUBLICATIONS

H.J. Elvik & L.R. Melatti; "Magnetic Ground Strap Connector"; Technical Digest No. 76, Mar. 1985, p. 21.

(Continued)

*Primary Examiner*—Stephen W Jackson
*Assistant Examiner*—Terrence R Willoughby
(74) *Attorney, Agent, or Firm*—Stetina Brunda Garred & Brucker

(57) ABSTRACT

There is provided an electrically conductive bracelet including an electrically conductive clasp member that is connectable to an electrical ground. A conductive metal band is connected to the clasp member to define a bracelet inner diameter. The conductive metal band includes a plurality of bar members. Each bar member includes a bar inner surface and a bar outer surface. The plurality of bar inner surfaces collectively define a band inner periphery and the plurality of bar outer surfaces collectively define a band outer periphery. The band inner periphery is positionable on a user to electrically connect the conductive metal band to the user. The band inner periphery is disposed between the band outer periphery and the user when the conductive metal band is disposed on the user. An electrically insulating cover is disposed over the band outer periphery for electrically insulating the band outer periphery.

20 Claims, 2 Drawing Sheets

U.S. PATENT DOCUMENTS

| | | | |
|---|---|---|---|
| 3,832,841 | A | 9/1974 | Cole |
| 3,851,456 | A | 12/1974 | Hamada |
| 3,857,397 | A | 12/1974 | Brosseau |
| 3,904,929 | A | 9/1975 | Kanaya et al |
| 3,949,129 | A | 4/1976 | Hubbard |
| 3,986,530 | A | 10/1976 | Maekawa |
| 3,987,613 | A | 10/1976 | Woods |
| 4,025,964 | A | 5/1977 | Owens |
| 4,112,941 | A | 9/1978 | Larimore |
| 4,211,456 | A | 7/1980 | Sears |
| 4,267,233 | A | 5/1981 | Tanaka |
| 4,321,789 | A | 3/1982 | Dammann |
| 4,373,175 | A | 2/1983 | Mykkanen |
| 4,398,277 | A | 8/1983 | Christiansen |
| 4,402,560 | A | 9/1983 | Swainbank |
| 4,420,529 | A | 12/1983 | Westhead |
| 4,422,483 | A | 12/1983 | Zins |
| 4,453,294 | A | 6/1984 | Morita |
| 4,459,633 | A | 7/1984 | Vandermark |
| 4,475,141 | A | 10/1984 | Antonevich |
| 4,577,256 | A | 3/1986 | Breidegam |
| 4,639,825 | A | 1/1987 | Breidegam |
| 4,654,748 | A | 3/1987 | Rees |
| 4,676,561 | A | 6/1987 | Barrett, II |
| 4,847,729 | A | 7/1989 | Hee |
| 4,878,148 | A | 10/1989 | Hee |
| 5,004,425 | A | 4/1991 | Hee |
| 5,184,274 | A * | 2/1993 | Weiss .......................... 361/220 |
| 6,215,639 | B1 | 4/2001 | Hee |
| 6,707,659 | B2 | 3/2004 | Hee |
| 6,866,128 | B2 * | 3/2005 | Moore et al. ............... 191/12.4 |

FOREIGN PATENT DOCUMENTS

| | | |
|---|---|---|
| DE | 3622948 | 1/1988 |
| GB | 791199 | 2/1958 |
| GB | 1067260 | 5/1967 |

OTHER PUBLICATIONS

Simco; ESD Control Products—Trustat Footwear and Grounding Accessories/Field Service Kit, p. 39 and Trustat Conductive Wrist Straps and Ground Leads, p. 40; copyright 1993.

Westek Electrostatics; "Personnel Grounding"; p. 7 no date.

* cited by examiner

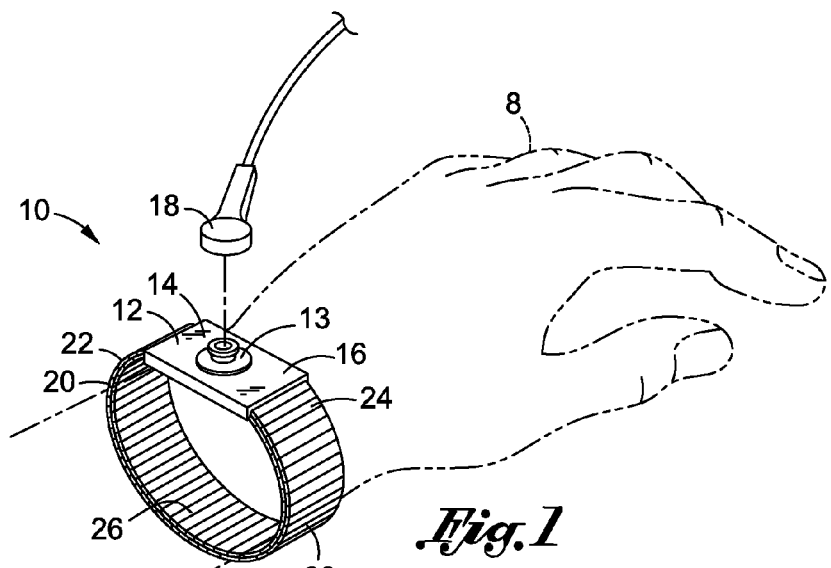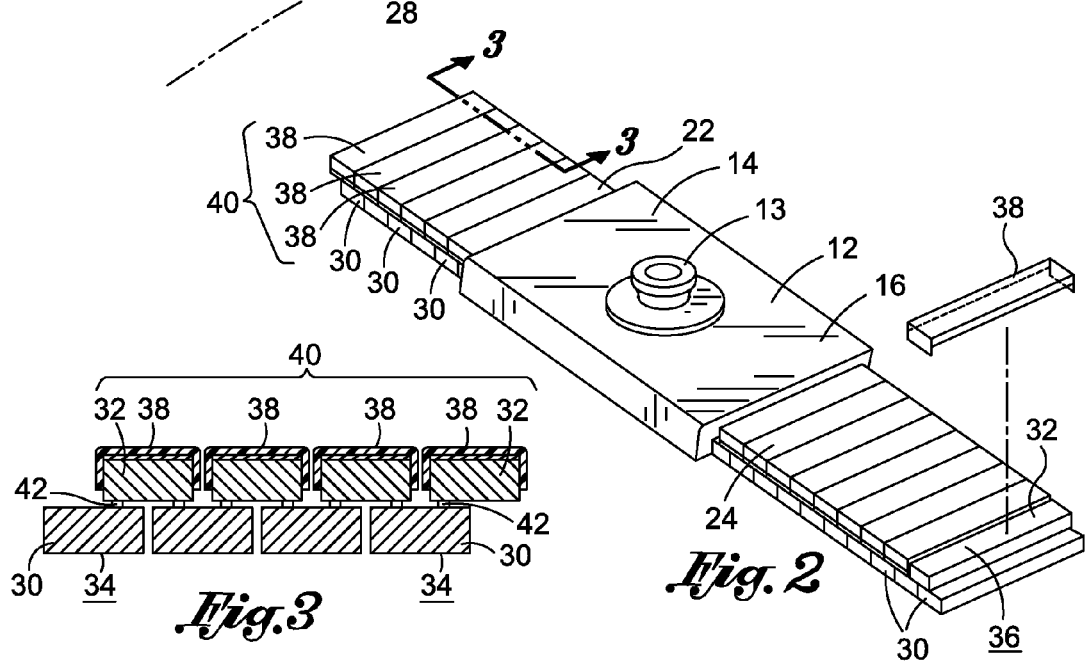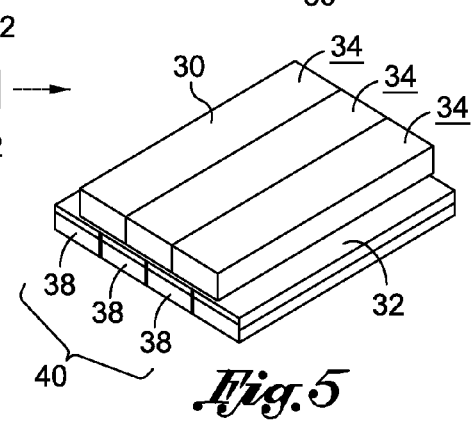

INSULATED METAL GROUNDING BRACELET

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

1. Field of the Invention

The present invention relates generally to electrically conductive bracelets and more specifically to an electrically conductive bracelet having an electrically conductive inner surface and an electrically insulated outer surface.

2. Description of the Related Art

The routine handling of static-sensitive electronic components is plagued by problems related to static electricity. A discharge of static electricity may damage sensitive electronics, particularly integrated circuits and other microelectronic components. An over-voltage of the static electricity may disable or destroy such electrical components. Such damage may be caused by a small electrical discharge. For instance, certain junctions within the components may be destroyed by as little as a 50-volt potential.

An individual may easily generate large amounts of static electricity while performing simple day-to-day activities. For instance, a person walking on a carpet on a dry day may accumulate as much as 30,000 volts of potential. An individual may additionally generate thousands of volts of potential by simply changing his position in his chair or handling a polystyrene foam cup.

A person who has generated static electricity may inadvertently discharge the static electricity into an electrical component through accidental contact or touching. Accordingly, it is common practice for personnel in industries in which electrical components are frequently handled or assembled to take measures to limit the discharge of static electricity into the components. Such a discharge may be prevented by keeping the worker at a zero electrical potential.

A grounding band is a tool that may be helpful in keeping the worker at or near a zero electrical potential. A typical grounding band includes a conductive surface that is electrically connectable to the wearer. Many grounding bands achieve such an electrical connection by placing the conductive surface in contact with the wearer's skin. The conductive surface is typically electrically connected to a grounding cord which leads from the band to a grounded electrical connection. Therefore, the electric charge is dissipated from the user to ground.

Many grounding bands are commonly constructed from a fabric material. An electrically conductive thread is typically included within an inner surface of the grounding band and may be brought into electrical communication with the wearer. The fabric grounding band may additionally include a fabric outer surface which may insulate the wearer from electrical shock in the event that the band came in contact with a live or ungrounded electrical instrument, which are commonly found in the production place of the electrical industry.

Although a fabric grounding band may initially serve as a sufficient tool for keeping a worker at or near a zero electrical potential, repeated use may reduce the effectiveness of the band. More specifically, dirt and sweat may insulate the electrically conductive thread from the user's skin. Therefore, electrical communication between the user and the electrically conductive band tends to be disrupted by the dirt and sweat.

Furthermore, certain electronics require handling in a controlled environment referred to herein as a clean room. Certain precautions are taken in order to reduce the number of airborne particles within the clean room. For instance, air flow, temperature, pressure, and humidity may be carefully controlled in order to maintain the standards of the clean room. Airborne particles may be introduced into the clean room by people and equipment contained therein. As such, additional measures may be taken in order to limit airborne particles introduced via people and equipment.

Fabric grounding bands discussed above tend to introduce contaminating particles into such an ultra clean environment. For instance, the fabric may rip and fray, thereby creating airborne particles which may be potentially hazardous in a clean room environment. In addition, the fabric may easily become contaminated or stained, which may also create problems within the clean room, such as quality control issues and high rejection rates.

Therefore, most grounding bands used in clean rooms are constructed from metal. Most metal bands that are used in a clean room are constructed from stainless steel to mitigate the development of stains on the band. Metal is a highly conductive material, which makes it a suitable material for use in the grounding band. However, if the metal is exposed, a dangerous conductive path may be created which may create a dangerous electrical shock if it comes in contact with a live or ungrounded electrical instrument, which is commonly found in the production place in the electronic industry.

Some metal bands include a layer of paint disposed on the outer surface to insulate the band and mitigate electrical shock of the wearer. However, stainless steel tends to be difficult to paint due to the presence of an oxide layer. In addition, any sharp corners located on the band make it difficult to paint.

Therefore, as is apparent from the foregoing, there exists a need in the art for an improved electrically conductive band which facilitates electrical protection from an electrical shock.

BRIEF SUMMARY OF THE INVENTION

According to an aspect of the present invention, there is provided an electrically conductive bracelet. The bracelet includes an electrically conductive clasp member connected to an electrically conductive metal band. The clasp member includes opposing first and second clasp end portions and is connectable to an electrical ground. A conductive metal band is connected to the clasp member. The band includes opposing first and second band end portions. The first band end portion is electrically and mechanically connected to the first clasp end portion and the second band end portion is electrically and mechanically connected to the second clasp end portion to define a bracelet inner diameter. The conductive metal band includes a plurality of bar members. Each bar member includes a contact surface and an exterior surface. The plurality of contact surfaces collectively define a band inner periphery and the plurality of exterior surfaces collectively define a band outer periphery. The band inner periphery is positionable on a user to electrically connect the conductive metal band to the user. The band inner periphery is disposed between the band outer periphery and the user when the conductive metal band is disposed on the user. An electrically insulating cover is disposed over the band outer periphery for electrically insulating the band outer periphery.

An aspect of the present invention includes an electrically conductive bracelet that includes an insulating layer that inhibits electrical shock of the wearer if the band comes in contact with live or ungrounded electronic equipment. The electrically insulating cover may be configured for use in a clean room environment. In this regard, the electrically insulating cover may be cleaned to remove potentially contaminating particles therefrom. Furthermore, the electrically insulating cover may be configured to mitigate the shedding of potentially contaminating particles within the clean room. It is contemplated that the electrically insulating cover may be comprised of a plastic material, such as acrylonitrile butadiene styrene (ABS), polyvinyl chloride (PVC) or polytetrafluoroethylene.

The electrically insulating cover may be comprised of a plurality of cover elements. Each cover element may be disposed over a respective one of the plurality of bar outer surfaces.

The conductive metal band may include a plurality of electrically conductive inner bar members and a plurality of electrically conductive outer bar members. Each inner bar member may include a contact surface, and each outer bar member may include an exterior surface. The plurality of interior surfaces may collectively define the band inner periphery, while the plurality of exterior surfaces may collectively define the band outer periphery. The conductive metal band may additionally include a plurality of electrically conductive connectors to connect the inner and outer bar members. Each outer bar member may be electrically and mechanically connected to two connectors which are electrically and mechanically connected to respective ones of the plurality of inner bar members. The electrically conductive clasp member may be electrically connected to the conductive metal band through the plurality of inner and outer bar members and the plurality of connectors.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings in which like numbers refer to like parts throughout and in which:

FIG. 1 is a top perspective view of an electrically conductive bracelet constructed in accordance with the present invention, the electrically conductive bracelet includes an electrically conductive clasp member and an electrically conductive band, the electrically conductive bracelet being positioned on a wrist of a user shown in phantom;

FIG. 2 is an enlarged top perspective view of a section of the electrically conductive band illustrated in FIG. 1, the electrically conductive band includes a plurality of inner bar members and a plurality of outer bar members, each outer bar member having an electrically insulating cover disposed over an exterior surface thereof;

FIG. 3 is a side cutaway view of the electrically conductive bracelet shown in FIG. 2, the electrically conductive band being in a contracted position;

FIG. 4 is a side cutaway view of the electrically conductive bracelet shown in FIG. 3, the electrically conductive band being in an expanded position;

FIG. 5 is a bottom perspective view of a portion of the electrically conductive band;

DETAILED DESCRIPTION OF THE INVENTION

Figure 6:
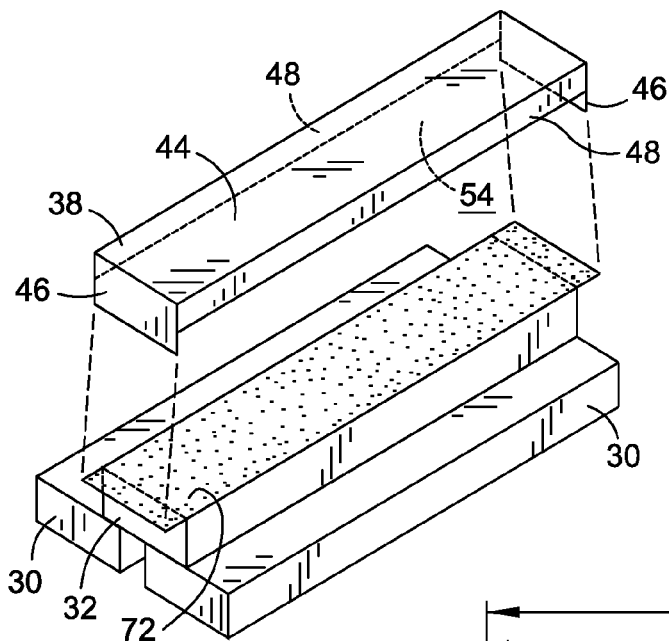
FIG. 6 is an exploded top perspective view of a portion of the electrically conductive band, wherein a cover element is positioned on an exterior surface of an outer bar member.

Referring now to the drawings wherein the showings are for purposes of illustrating a preferred embodiment of the present invention only, and not for purposes of limiting the same, FIGS. 1-10 illustrate an electrically conductive bracelet 10 constructed in accordance with the present invention. The electrically conductive bracelet 10 is worn by a user 8 to dissipate electricity away from the user 8. As shown in FIG. 1, the electrically conductive bracelet 10 is positioned on the wrist of a user 8, shown in phantom. However, it is understood that the bracelet 10 may be configured for use on another appendage, such as a user's ankle.

According to an aspect of the present invention, the bracelet 10 includes an electrically conductive clasp member 12 and an electrically conductive metal band 20. The clasp member 12 is connectable to an electrical ground to dissipate electrical energy from the clasp member 12 to the electrical ground. The electrical ground may include a grounding wire 18 which is connectable with the clasp member 12. The clasp member 12 illustrated in FIGS. 1 and 2 includes a clasp fastener 13 which connects with the grounding wire 18. The grounding wire 18 may include a complimentary grounding fastener which engages with the clasp fastener 13 to mechanically and electrically connect the grounding wire 18 to the clasp member 12. The grounding fastener and clasp fastener 13 may be traditional snap fasteners or other connectors known by those skilled in the art.

The clasp member 12 includes opposing first and second clasp end portions 14, 16. Likewise, the electrically conductive band 20 includes opposing first and second band end portions 22, 24. The first clasp end portion 14 is electrically and mechanically connected to the first band end portion 22, and the second clasp end portion 16 is electrically and mechanically connected to the second band end portion 24. In one embodiment, the first and second clasp end portions 14, 16 are detachably connected to the first and second band end portions 22, 24 to facilitate quick and easy removal of the clasp member 12 from the band 20. This may be desirable if the band 20 or clasp member 12 requires repair or replacement. A new band 20 or clasp member 12 may be connected to an existing band 20 or clasp member 12. However, in another embodiment, the connection between the band 20 and the clasp member 12 is more permanent, as shown in FIG. 1. To this end, donning of the bracelet 10 upon a wearer 8 may not require detaching the band 20 from the clasp member 12. Known means of connecting the band 20 to the clasp member 12 may be used without departing from the spirit and scope of the present invention.

When the first and second clasp end portions 14, 16 are connected to the first and second band end portions 22, 24, a continuous loop is formed. In this manner, the clasp member 12 and the band 20 collectively define a bracelet inner periphery 26. Electrical current may pass along the loop from the band 20 to the clasp 12 and ultimately to the electrical ground.

According to one aspect of the invention the electrically conductive metal band 20 includes a plurality of inner bar members 30 and a plurality of outer bar members 32, as best shown in FIGS. 1-9. Each inner bar member 30 includes a contact surface 34 and each outer bar member 32 includes an exterior surface 36. The plurality of contact surfaces 34 collectively define the band inner periphery 26 and the plurality of exterior surfaces 36 collectively define the band outer periphery 28. The band inner periphery 26 is positionable on a user 8 to electrically connect the bracelet to the user 8. Therefore, electrical buildup on the user 8 may be electrically communicated to the bracelet 10 via the inner periphery 16.

The inner and outer bar members 30, 32 may be electrically and mechanically connected to each other via electrically conductive connectors 42. As shown in FIGS. 3 and 4, each outer bar member 32 is connected to two connectors 42, each of which is connected to respective ones of the plurality of inner bar member 30. Therefore, electrical current may pass between the inner and outer bar members 30, 32 via the connectors 42. Furthermore, the clasp member 12 may be electrically connected to the metal band 20 via the plurality of inner and outer bar members 30, 32 and the plurality of connectors 42.

The electrically conductive bracelet 10 further includes an electrically insulating cover 40 to guard the wearer 8 against inadvertent electrical shock. As used herein, the term "electrically insulating" of "electrically insulation cover" 40 refers to being substantially electrically non-conductive in comparison to the band 20. In this manner, the electrically insulating cover 40 mitigates electrical current from entering the band 20 through the outer periphery 28. In this regard, the electrically insulating cover 40 is disposed over the band outer periphery 28. Therefore, if a wearer 8 accidentally places the band 20 in contact with an ungrounded electronic instrument, the insulating cover 40 restricts electrical current from entering the band 20 through the band outer periphery 28. In this manner, the wearer 8 is protected from electrical shock. Although the electrically insulating cover 40 tends to mitigate inadvertent electrical shock to the wearer 8, an antistatic chemical may be applied to the cover 40 to reduce the amount of static generation in circumstances which warrant further protection.

According to various aspects of the invention, the electrically insulating cover 40 is comprised of a plurality of cover elements 38. Each cover element 38 is disposed over a respective one of the plurality of exterior surfaces 36. It may be desirable to configure each exterior surface 36 to be flat in order to facilitate engagement between the cover element 38 and the respective exterior surface 36. A flat exterior surface 36 may provide a clean, tight fit with the cover element 38. However, other aspects of the present invention may include bracelets 10 having rounded exterior surfaces 36.

Figure 7:
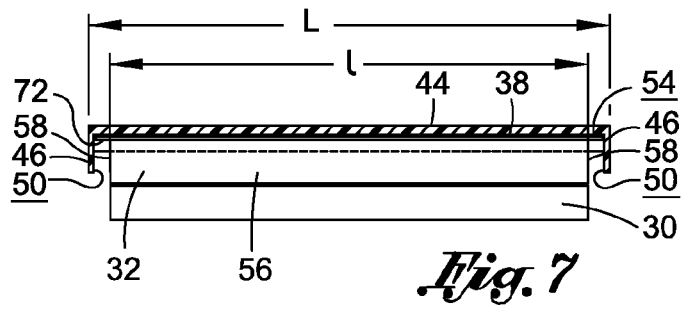
FIG. 7 is a side elevation view of the electrically conductive band shown in FIG. 6, the cover element being disposed on the exterior surface of the outer bar member.
Figure 9:
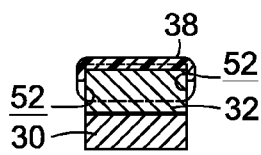
FIG. 9 is an end portion view of the electrically conductive band shown in FIG. 8.
Figure 8:
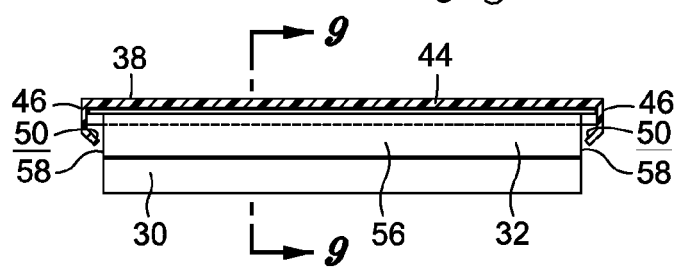
FIG. 8 is a side elevation view of the electrically conductive band shown in FIG. 7, the cover element having end faces folded toward the outer bar member to secure the cover element thereto.

Referring now to FIGS. 6-8, the cover elements 38 include a cover upper face 44 that is disposed over the exterior surface 36 of the outer bar member 32. It is understood that minimal insulative protection may be achieved by providing a cover element 38 solely comprised of the cover upper face 44. However, it may be desirable to provide cover side flaps 48 and cover end flaps 46 to provide enhanced insulative protection. The cover side flaps 48 of a respective cover element 38 may be disposed over bar side faces 56 of a respective outer bar member 32. Likewise, the cover end flaps 46 of a respective cover element 38 may be disposed over respective bar end faces 58 of the outer bar member 32.

Each cover element 38 may be disposed directly onto the outer bar member 32, as shown in FIG. 2. Alternatively, an adhesive layer 72 may be disposed between the cover element 38 and the outer bar member 32, as best shown in FIG. 6. The length of the adhesive layer 72 may be longer than the length "l" of the exterior surface 36. Therefore, when the cover element 38 is positioned over the outer bar member 32, portions of the adhesive layer 72 may be disposed between the end flaps 46 of the cover element 38 and the bar end faces 58 of the outer bar member 32. In addition, the width of the adhesive layer 72 may be wider than the width of the exterior surface to enable portions of the adhesive layer 72 to be disposed between the cover side flap 48 and the bar side face 56.

In addition to the foregoing, it is contemplated that various aspects of the present invention include an electrically conductive band 20 that is expandable. In other words, the electrically conductive band 20 may be configured to enable expansion and contraction of the band inner periphery 26. This may be beneficial to slip the band 20 onto the desired appendage of the wearer 8 for use. For instance, as shown in FIG. 1, the band 20 is worn on the wrist of a wearer 8. Consequently, the band 20 may expand to slide over the wearer's hand and subsequently contract to fit on the wearer's wrist.

In one embodiment, expansion is achieved through spring-biased connectors 42. For instance, the band 20 shown in FIGS. 3 and 4 includes such spring biased connectors 42 which allows the band 20 to expand between expanded and contracted positions. Upon expansion of the band 20, the spring-biased connectors 42 urge the band 20 back into the contracted position. In FIG. 3, the band 20 is in the contracted position, whereas in FIG. 4, the band 20 is in the expanded position. The size of the band inner periphery 26 is smaller when the band 20 is in the contracted position, compared to the size of the band inner periphery 26 when the band 20 is in the expanded position. In the case of expandable bracelets 10 including both inner and outer bar members 30, 32, the distance between adjacent outer bar members 32 is larger when the bracelet 10 is in the expanded position than the distance between the same adjacent outer bar members 32 in the contracted position. Similarly, the distance between adjacent inner bar members 30 is larger in the expanded position than the distance between the same adjacent inner bar members 30 in the contracted position.

In one embodiment, the spring biased connectors 42 may be pivotally connected to the inner and outer bar members 30, 32. The embodiment depicted in FIGS. 3 and 4 includes connectors 42 which pivot relative to the inner and outer bar members 30, 32 as the band 20 expands and contracts. As shown, the connectors 42 are substantially perpendicular to the inner and outer bar members 30, 32 when the band 20 is in the contracted position. As the band 20 expands, the connectors 42 move from a substantially perpendicular orientation and into an angular orientation relative to the inner and outer bar members 30, 32.

It is also contemplated that the spring-biased connectors 42 may be translatably connected to the inner and outer bar members 30, 32. For instance, a portion of the connector 42 may translate in a slot within one of or both of the inner or outer bar members 30, 32 to facilitate expansion or contraction of the band 20. The connector 42 may be translatably connected to one or both of the inner and outer bar members 30, 32.

Figure 10:
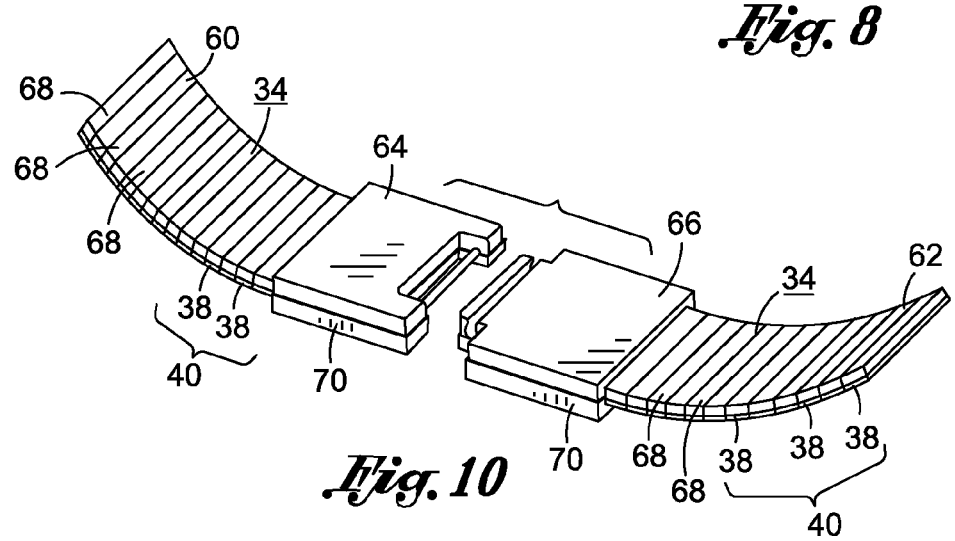
FIG. 10 is a top perspective view of an electrically conductive bracelet having an electrically conductive band comprised of a plurality of bar members.

Although the foregoing describes the band 20 as including inner and outer bar members 30, 32, it is contemplated that various aspects of the invention include a band 20 comprised of a single "layer" of bar members 68 as shown in FIG. 10. The bar members 68 include a contact surface 34 (similar to the inner bar members 30 described above) and an exterior surface 36 (similar to the outer bar members 32 described above). The plurality of contact surfaces 34 collectively define the band inner periphery 26, and the plurality of exterior surfaces 36 collectively define the band outer periphery 28, as described above in more detail. An insulating cover 40 is disposed over the outer periphery of the band 20.

As shown in FIG. 10, the band 20 is comprised of first and second band portions 60, 62 and complimentary first and second fasteners 64, 66. The first fastener 64 is connected to a first band portion 60 and the second fastener 66 is connected to the second band portion 62. The complimentary first and second fasteners 64, 66 may be selectively connectable/detachable to secure the band 20 to the wearer 8. In this regard, it may not be necessary to configure the band 20 to be expandable to allow for donning and removal of the bracelet 10. Instead, the first and second fasteners 64, 66 may enable such donning and removal of the bracelet 10 on the user 8. However, it is understood that an expandable band 20 with only one layer of bar members 68 may be used without departing from the spirit and scope of the present invention.

In order to maintain the insulative protection offered by the electrically insulating cover 40, the first and second fasteners 64, 66 may include fastener insulating covers 70 disposed on the exterior thereof. The fastener insulating cover 70 may be applied to the first and second fasteners 64, 66 in a manner similar to that described above in relation the cover elements 38. Likewise, an insulating cover may be applied to portions of the electrically conductive clasp member 12 to mitigate electrical shock of the wearer 8.

According to other aspects of the invention, the bracelet 10 is configured for use in a clean room. As used herein, a clean room is a controlled environment that is commonly used for handling sensitive electrical equipment. In general, the concentration of airborne particles within the clean room is controlled within specified limits. As an illustration, in a typical office building, the air may contain as many as 500,000 to 1,000,000 particles per cubic foot of air. However, a Class 100 clean room may be designed to keep the concentration of air particles at or below 100 particles per cubic foot of air. Likewise, a Class 1,000 clean room may be configured to maintain the concentration at or below 1,000 particles per cubic feet of air. Contaminants may be introduced into a clean room by people, processes, facilities, and equipment. As such, particles may be continually removed from the air in order to maintain the airborne particle concentration within the specified clean room standards. Air flow rates, air flow direction, temperature, humidity, pressurization and filtration may be controlled to reduce the number of particles within the clean room. Furthermore, additional precautions may be taken to limit the number of potentially contaminating particles introduced by equipment brought into the clean room, such as the bracelet 10. For instance, it may be beneficial to use equipment which is configured to mitigate the number of particles it may shed. Additionally, materials which may be resistant to staining may also be preferred. Consequently, various aspects of the present invention are directed toward providing an electrically conductive bracelet 10 having an electrically insulating cover 40 which may be used in a clean room.

As is apparent from the forgoing, it is typically important to reduce the number of contaminating particles introduced into the clean room. This may be achieved by fabricating the bracelet 10 out of materials which tend to resist the shedding of particles. The band 20 may be comprised of a stainless metal to mitigate staining thereof, which may contaminate the clean room. The electrically insulating cover 40 may be comprised of a variety of different materials. The electrically insulating cover 40 may be comprised of a substantially electrically non-conductive polymer, including but not limited to plastic materials. Exemplary plastic materials may include polyvinyl chloride, acrylonitrile butadiene styrene, or polytetrafluoroethylene, which is manufactured by E.I. du Pont de Nemours and Company and sold under the trademark TEFLON. Plastic materials may be ideal because they may be cleaned to remove potentially contaminating particles before being introduced into the clean room. In addition, plastic materials are less prone to having particles flake off during use. Furthermore, plastic materials may be recyclable, which may make them environmentally friendly. It is noted that although the foregoing discusses plastic as a material that may be used to fabricate the insulating cover 40, other materials known by those skilled in the art, such as rubber or silicon, may also be used without departing from the spirit and scope of the present invention.

In addition to the foregoing, there is provided a method for installing an electrically insulating cover 40 to an electrically conductive bracelet 10. It is contemplated that the electrically insulating cover 40 may be installed during the initial manufacture of the electrically conductive bracelet 10 via injection forming or vacuum forming. As mentioned earlier, the electrically insulating cover 40 may include a plurality of cover elements 38. Each cover element 38 may include a cover upper face 44, a pair of opposing cover end flaps 46, and a pair of opposing cover side flaps 48. The cover upper face 44 includes a face outer surface and a face inner surface 54. Each cover end flap 46 includes an end inner surface 50 and an end outer surface. Likewise, each cover side flap 48 includes a side inner surface 52 and a side outer surface. Each cover element 38 is disposed over a respective exterior surface 36. It is understood that the cover element 38 may be disposed over a bar member 68, or an outer bar member 32. According to one embodiment, the inner surface 54 of the cover upper face 44 is disposed in abutting contact with the exterior surface 36. In another embodiment, the adhesive layer 72 is disposed between the exterior surface 36 and the cover element 38.

FIG. 7 is a side view of a cover element 38 disposed on an outer bar member 32, As shown, the length "L" of the cover upper face 44 may be greater than the length l of the exterior surface 36. Consequently, the opposing cover end flaps 46 may not abut the bar end faces 58. However, each cover end flap 46 is disposed in close proximity to a respective one of the bar end faces 58. Subsequently, the cover end flaps 46 are bent toward the bar end faces 58 as shown in FIG. 8. This may be accomplished by methods known by those skilled in the art, including vacuum forming or heat treatment.

The opposing cover side flaps 48 may be configured to fit snugly over respective ones of the bar side faces 56 when the cover element 38 is initially disposed on the bar member 68, 32. However, the opposing cover side flaps 48 may also require tightening similar to the opposing cover end flaps 46.

It is understood that the cover elements 38 may be applied to electrically conductive bracelets 10 that include only one layer of bar members 68 as best illustrated in FIG. 10. Alternatively, the cover elements 38 may be applied to electrically conductive bracelets 10 that include both inner bar members 30 and outer bar members 32 as shown in FIGS. 1 through 9. In the case of electrically conductive bracelets 10 only comprising of one layer of bar members 68, a cover element 38 is disposed over each bar member 68.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intend portioned to be limited to the specific combination described herein. Thus, the scope of the claims is not to be limited by the illustrated embodiments.

What is claimed is:

1. An electrically conductive bracelet comprising:
   an electrically conductive clasp member having opposing first and second clasp end portions, the electrically conductive clasp member being electrically connectable to an electrical ground;
   an electrically conductive metal band having opposing first and second band end portions, the first band end portion being electrically and mechanically connected to the first clasp end portion and the second band end portion being electrically and mechanically connected to the second clasp end portion to define a bracelet inner circumference, the electrically conductive metal band including a plurality of bar members, each bar member having a contact surface and an exterior surface, the plurality of contact surfaces collectively defining a band inner periphery and the plurality of exterior surfaces collectively defining a band outer periphery, the band inner periphery being positionable on a user to electrically connect the electrically conductive metal band to the user, the band inner periphery being disposed between the band outer periphery and the user when the electrically conductive metal band is disposed on the user; and
   an electrically insulating cover disposed over the band outer periphery for electrically insulating the band outer periphery.

2. The electrically conductive bracelet as recited in claim 1, wherein the electrically insulating cover includes a plurality of cover elements, each cover element being disposed over a respective one of the plurality of bar outer surfaces.

3. The electrically conductive bracelet as recited in claim 1, wherein the electrically conductive metal band is expandable.

4. The electrically conductive band as recited in claim 1, wherein the electrically insulating cover is comprised of a non-conductive polymer.

5. The electrically conductive band as recited in claim 4, wherein the non-conductive polymer is a plastic material.

6. The electrically conductive band as recited in claim 5, wherein the plastic material is polyvinyl chloride.

7. The electrically conductive band as recited in claim 5, wherein the plastic material is acrylonitrile butadiene styrene.

8. The electrically conductive band as recited in claim 5, wherein the plastic material is polytetrafluoroethylene.

9. An electrically conductive bracelet comprising:
   an electrically conductive clasp member having opposing first and second clasp end portions, the clasp member being electrically connectable to an electrical ground;
   an electrically conductive metal band having opposing first and second band end portions, the first band end portion being electrically and mechanically connected to the first clasp end portion and the second band end portion being electrically and mechanically connected to the second clasp end portion to define a bracelet inner diameter, the electrically conductive metal band including:
      a plurality of electrically conductive inner bar members, each inner bar member having a contact surface, the plurality of contact surfaces collectively defining the band inner periphery, the band inner periphery being positionable on a user to electrically connect the conductive metal band to the user;
      a plurality of electrically conductive outer bar members, each outer bar member having an exterior bar surface, the plurality of exterior bar surfaces collectively defining the band outer periphery, the band inner periphery being disposed between the band outer periphery and the user when the conductive metal band is disposed on the user; and
      a plurality of electrically conductive connectors, each outer bar member being electrically and mechanically connected to two connectors which are electrically and mechanically connected to respective ones of the plurality of inner bar members; and
   an electrically insulating cover disposed over the band outer periphery for electrically insulating the band outer periphery.

10. The electrically conductive bracelet as recited in claim 9, wherein the electrically insulating cover includes a plurality of cover elements, each cover element being disposed over a respective one of the plurality of exterior bar surfaces.

11. The electrically conductive bracelet as recited in claim 9, wherein the electrically conductive metal band is expandable.

12. The electrically conductive bracelet as recited in claim 9, wherein the electrically conductive clasp member is electrically connected to the conductive metal band through the plurality of inner and outer bar members and the plurality of connectors.

13. The electrically conductive band as recited in claim 9, wherein the plurality of electrically conductive connectors are spring-biased connectors.

14. The electrically conductive band as recited in claim 13, wherein the plurality of electrically conductive connectors are pivotally connected to the plurality of electrically conductive inner bar members.

15. The electrically conductive band as recited in claim 13, wherein the plurality of electrically conductive connectors are pivotally connected to the plurality of electrically conductive outer bar members.

16. The electrically conductive band as recited in claim 9, wherein the electrically insulating cover is comprised of a non-conductive polymer.

17. The electrically conductive band as recited in claim 16, wherein the non-conductive polymer is a plastic material.

18. The electrically conductive band as recited in claim 17, wherein the plastic material is polyvinyl chloride.

19. The electrically conductive band as recited in claim 17, wherein the plastic material is acrylonitrile butadiene styrene.

20. The electrically conductive band as recited in claim 17, wherein the plastic material is polytetrafluoroethylene.

* * * * *